United States Patent
Xu et al.

(10) Patent No.: US 9,944,587 B2
(45) Date of Patent: Apr. 17, 2018

(54) PROCESS FOR VAPOR-PHASE METHANOL CARBONYLATION TO METHYL FORMATE, A CATALYST USED IN THE PROCESS AND A METHOD FOR PREPARING THE CATALYST

(71) Applicant: FUJIAN INSTITUTE OF RESEARCH ON THE STRUCTURE OF MATTER, CHINESE ACADEMY OF SCIENCES, Fuzhou (CN)

(72) Inventors: Zhongning Xu, Fuzhou (CN); Guocong Guo, Fuzhou (CN); Siyan Peng, Fuzhou (CN); Zhiqiao Wang, Fuzhou (CN); Qingsong Chen, Fuzhou (CN); Mingsheng Wang, Fuzhou (CN); Yuangen Yao, Fuzhou (CN)

(73) Assignee: FUJIAN INSTITUTE OF RESEARCH ON THE STRUCTURE OF MATTER, CHINESE ACADEMY OF SCIENCES, Fuzhou, Fujian (CN)

( * ) Notice: Subject to any disclaimer, the term of this patent is extended or adjusted under 35 U.S.C. 154(b) by 0 days.

(21) Appl. No.: 15/110,072

(22) PCT Filed: Jun. 12, 2014

(86) PCT No.: PCT/CN2014/079732
§ 371 (c)(1),
(2) Date: Jul. 6, 2016

(87) PCT Pub. No.: WO2015/103851
PCT Pub. Date: Jul. 16, 2015

(65) Prior Publication Data
US 2016/0332953 A1 Nov. 17, 2016

(30) Foreign Application Priority Data

Jan. 7, 2014 (CN) .......................... 2014 1 0006815
Jan. 7, 2014 (CN) .......................... 2014 1 0007283

(51) Int. Cl.
| | | |
|---|---|---|
| C07C 67/36 | (2006.01) | |
| B01J 23/89 | (2006.01) | |
| B01J 37/08 | (2006.01) | |
| B01J 37/16 | (2006.01) | |
| B01J 37/34 | (2006.01) | |
| B01J 21/04 | (2006.01) | |
| B01J 21/10 | (2006.01) | |
| B01J 21/06 | (2006.01) | |
| B01J 21/08 | (2006.01) | |
| B01J 21/18 | (2006.01) | |
| B01J 23/02 | (2006.01) | |
| B01J 23/06 | (2006.01) | |
| B01J 23/44 | (2006.01) | |

(Continued)

(52) U.S. Cl.
CPC .............. *C07C 67/36* (2013.01); *B01J 21/04* (2013.01); *B01J 21/063* (2013.01); *B01J 21/066* (2013.01); *B01J 21/08* (2013.01); *B01J 21/10* (2013.01); *B01J 21/18* (2013.01); *B01J 23/02* (2013.01); *B01J 23/06* (2013.01); *B01J 23/40* (2013.01); *B01J 23/44* (2013.01); *B01J 23/462* (2013.01); *B01J 23/464* (2013.01); *B01J 23/466* (2013.01); *B01J 23/468* (2013.01); *B01J 23/89* (2013.01); *B01J 23/892* (2013.01); *B01J 23/8906* (2013.01); *B01J 23/8913* (2013.01); *B01J 23/8926* (2013.01); *B01J 35/006* (2013.01); *B01J 35/0013* (2013.01); *B01J 35/023* (2013.01); *B01J 37/0201* (2013.01); *B01J 37/088* (2013.01); *B01J 37/16* (2013.01); *B01J 37/343* (2013.01)

(58) Field of Classification Search
CPC ...................................................... C07C 67/36
See application file for complete search history.

(56) References Cited

U.S. PATENT DOCUMENTS

| 4,420,633 A | 12/1983 | Furusaki et al. | |
|---|---|---|---|
| 4,792,620 A * | 12/1988 | Paulik ................ | B01J 31/0231 560/232 |
| 2009/0286899 A1 * | 11/2009 | Hofmann ............. | B01J 21/063 522/99 |

FOREIGN PATENT DOCUMENTS

| CN | 1053019 A | 7/1991 |
|---|---|---|
| CN | 1160601 A | 10/1997 |

(Continued)

OTHER PUBLICATIONS

Norskov et al, Nature Chemistry, Towards the Computational Design of Solid Catalysts, 2009, 1, pp. 37-46. (Year: 2009).*
International Search Report for International Application No. PCT/CN2014/079732 dated Aug. 26, 2014.
Vlasenko, et al., "Direct Single-Stage Conversion of Synthesis Gas to Dimethoxymethane: Influence of the Sequence of Metal Introduction into Cu, Pd-Zeolite Catalysts on the Degree of Cu and Pd Reduction and Catalyst Acidity," *Russian Journal of Applied Chemistry*, vol. 76, No. 10, pp. 1615-1619 (2003).
Wojcieszak, et al., "Direct Methyl Formate Formation from Methanol over Supported Palladium Nanoparticles at Low Temperature," *ChemCatChem*, vol. 5, pp. 339-348 (2013).
First Office Action issued for the parallel Chinese patent application No. 201410006815.0 dated Jun. 27, 2014.

(Continued)

*Primary Examiner* — Paul A Zucker
(74) *Attorney, Agent, or Firm* — Kilpatrick Townsend & Stockton LLP

(57) ABSTRACT

A process for vapor-phase carbonylation of methanol to methyl formate, whereby a feed gas containing methanol, carbon monoxide, hydrogen and oxygen is passed through a reactor loaded with a supported nano-scaled platinum group metal heterogeneous catalyst to produce methyl formate by a vapor-phase carbonylation reaction, under reaction conditions with a space velocity of 500-5000 $h^{-1}$, a temperature of 50-150° C. and a pressure of 0.01-2 MPa. Supported nano-scaled platinum group metal heterogeneous catalysts are prepared via ultrasonic dispersion and calcination. Methyl formate is produced and isolated under relatively mild conditions.

10 Claims, 1 Drawing Sheet

(51) Int. Cl.
*B01J 23/48* (2006.01)
*B01J 23/40* (2006.01)
*B01J 35/00* (2006.01)
*B01J 35/02* (2006.01)
*B01J 37/02* (2006.01)
*B01J 23/46* (2006.01)

(56) References Cited

FOREIGN PATENT DOCUMENTS

| | | | |
|---|---|---|---|
| CN | 1696101 | A | 11/2005 |
| CN | 101134163 | A | 3/2008 |
| CN | 101134163 | B * | 9/2010 |
| CN | 101985103 | A | 3/2011 |
| CN | 102553579 | A * | 8/2011 |
| CN | 102553579 | A | 7/2012 |
| CN | 102600879 | A | 7/2012 |
| CN | 103691451 | A | 4/2014 |
| CN | 103694116 | A | 4/2014 |
| JP | 2000167400 | A | 6/2000 |
| JP | 2001224970 | A | 8/2001 |
| JP | 2001288144 | A | 10/2001 |
| WO | 03/089398 | A1 | 10/2003 |

OTHER PUBLICATIONS

First Office Action issued for the parallel Chinese patent application No. 201410007283.2 dated Jun. 25, 2014.
Search Report issued for the parallel Chinese patent application No. 201410006815.0 dated Apr. 18, 2014.
Search Report issued for the parallel Chinese patent application No. 201410007283.2 dated Apr. 23, 2014.

* cited by examiner

PROCESS FOR VAPOR-PHASE METHANOL CARBONYLATION TO METHYL FORMATE, A CATALYST USED IN THE PROCESS AND A METHOD FOR PREPARING THE CATALYST

TECHNICAL FIELD

The present application relates to a process for producing methyl formate. The present application also relates to a catalyst for producing methyl formate and a method for preparing the catalyst.

BACKGROUND

Methyl formate is an extremely important intermediate in C1 chemistry, with a wide range of applications. Products such as formic acid, formamide, N, N-dimethylformamide, dimethyl carbonate, ethylene glycol, acetic acid, methyl acetate, acetic anhydride, methyl methacrylate, high purity CO, diphosgene and the like can be synthesized from methyl formate. Methyl formate can also be used as insecticides, pesticides, fumigants and tobacco processing agents. The consumption of methyl formate comprises as follows: synthetic leathers accounting for 30%, pesticides accounting for 26%, pharmaceuticals accounting for 25%, acrylonitrile accounting for 10%, others accounting for 9%. With the development of polyacrylonitrile fibers, polyurethane synthetic leathers, pharmaceutical industries and the like, the market demand for methyl formate will grow at a rate of 10% per annum.

Processes for producing methyl formate mainly include: methanol-formic acid esterification, liquid-phase methanol carbonylation, dehydrogenation of methanol, oxidative dehydrogenation of methanol, formaldehyde dimerization, direct synthesis from syngas, etc. Among them, industrialized processes are methanol-formic acid esterification, liquid-phase methanol carbonylation and dehydrogenation of methanol. Methanol-formic acid esterification has been eliminated because of backward technology, high energy consumption and serious equipment corrosion. As a new technology at present, dehydrogenation of methanol has not yet been applied in large scale industries. Currently liquid-phase methanol carbonylation is the main process used in industry. Since 1982, almost all of new plants in the world have been employing the technology of liquid-phase methanol carbonylation, which has become the main process for mass production of methyl formate.

Liquid-phase methanol carbonylation ($CH_3OH+CO=HCOOCH_3$) was first industrialized by BASF corporation, Germen, the only industrialized catalyst is sodium methoxide whose significant advantage is high selectivity, and methyl formate is the only product. However, the following serious disadvantages exist in using the sodium methoxide catalyst: (1) sodium methoxide is extremely sensitive to water, thus the demand for the purity of raw material is very high, wherein the contents of impurities such as $H_2O$, $CO_2$, $O_2$, sulfides and the like should be less than $10^{-6}$, and water content in methanol should also be less than $10^{-6}$; (2) sodium methoxide is a strong base and is severely corrosive to equipment; (3) the reaction is carried out in reaction kettle and belongs to homogeneous reaction, wherein the separation of catalyst from product is difficult; (4) the pressure of reaction is relatively high, which is about 4 MPa; (5) the solubility of sodium methoxide in methyl formate is relatively small, if, after the conversion of methanol was greater than a certain limit value, the sodium methoxide will form solid precipitate which will clog pipes and valves, bringing great difficulties to practical operation, and even normal production will be impossible.

Given the defects existing in the current process of liquid-phase methanol carbonylation, the present application discloses a process for vapor-phase methanol carbonylation to methyl formate and a catalyst used in the process. Methyl formate is synthesized on a supported nano-scaled platinum group metal heterogeneous catalyst instead of the sodium methoxide catalyst. The process and the catalyst disclosed by the present application have solved the technical problems in current industrial technology, such as high requirements for purity of raw materials, a severe corrosion of the equipment by a catalyst, a difficulty in separation for a catalyst from a product, a high reaction pressure, great difficulties in operation and so on, and provide a novel technical route for producing methyl formate.

DISCLOSURE OF INVENTION

To solve the abovementioned problems, the present application discloses a process for a vapor-phase carbonylation of methanol to methyl formate and a catalyst used in said process, having advantages of a good stability, easy separation from products, no corrosion to equipment, low requirements for the purity of the feed gas, a high conversion of CO, a high selectivity for methyl formate and so on.

In one aspect, provided is a process for vapor-phase carbonylation of methanol to methyl formate, in which a feed gas containing methanol, carbon monoxide, hydrogen and oxygen is passed through a reactor loaded with a supported nano-scaled platinum group metal heterogeneous catalyst to produce methyl formate by a vapor-phase carbonylation reaction, under reaction conditions with a space velocity of 500-5000 $h^{-1}$, a temperature of 50-150° C. and a pressure of 0.01-2 MPa.

In another aspect, provided is a supported nano-scaled platinum group metal heterogeneous catalyst for use in the process, comprising a nano-scaled platinum group metal active component and a carrier, wherein, the percentage content of the nano-scaled platinum group metal active component is 0.01-2%, preferably in the range of 0.1-1%, by mass of the carrier;

said nano-scaled platinum group metal active component is one metal or a mixture of two or more metals selected from ruthenium, rhodium, palladium, osmium, iridium, and platinum, or an alloy of two or more metals selected from ruthenium, rhodium, palladium, osmium, iridium, and platinum; and said carrier is one or more selected from alumina, silica, magnesia, zinc oxide, zirconia, titania, metal-organic framework compounds, activated carbon, molecular sieves, carbon nanotubes, and graphene.

In yet another aspect, provided is a method for preparing the catalyst, comprising the steps as follows:

a) placing a carrier into a solution containing a platinum group metal salt and a solvent, mixing uniformly, and removing the solvent in the presence of ultrasound wave;

b) drying the sample obtained from step a) at 100-200° C. for 1-20 hours, and calcining at 200-600° C. for 1-20 hours;

c) adding the sample obtained from step b) into a solution comprising a reductant, a capping agent, and a stabilizer, and carrying out a reduction reaction at 20-120° C.; and d) washing and drying the sample obtained from step c) in vacuum to obtain said supported nano-scaled platinum group metal heterogeneous catalyst.

Detailed Embodiments

Specifically, the present application discloses a process for a vapor-phase methanol carbonylation to methyl formate, characterized in that a feed gas containing methanol, carbon monoxide, hydrogen and oxygen is passed through a reactor loaded with a supported nano-scaled platinum group metal heterogeneous catalyst to produce methyl formate by a vapor-phase carbonylation reaction, under reaction conditions with a space velocity of 500-5000 $h^{-1}$, a temperature of 50-150° C. and a pressure of 0.01-2 MPa.

In one embodiment, said feed gas comprises 10-50% methanol, 10-50% carbon monoxide, 10-30% hydrogen and 5-20% oxygen, by volume percentage.

In one embodiment, said vapor-phase methanol carbonylation reaction is carried out in a fixed bed reactor.

In one embodiment, said vapor-phase methanol carbonylation reaction is carried out in multiple fixed bed reactors, and the fixed bed reactors are connected in series and/or in parallel manner.

The present application also discloses a supported nano-scaled platinum group metal heterogeneous catalyst used in the process for vapor-phase methanol carbonylation to methyl formate, characterized in that, said supported nano-scaled platinum group metal heterogeneous catalyst comprises a nano-scaled platinum group metal active component and a carrier; and the percentage content of the nano-scaled platinum group metal active component is 0.01-2%, by mass of the carrier.

Said nano-scaled platinum group metal active component is one metal or a mixture of two or more metals optionally selected from ruthenium, rhodium, palladium, osmium, iridium and platinum; or said nano-scaled platinum group metal active component is an alloy of two or more metals optionally selected from ruthenium, rhodium, palladium, osmium, iridium and platinum.

Said carrier is one or more carriers optionally selected from alumina, silica, magnesia, zinc oxide, zirconia, titania, metal-organic framework compounds, activated carbon, molecular sieves, carbon nanotubes, and graphene.

The nano-scaled platinum group metal active component in the present application refers to a platinum group metal as active component dispersed on a carrier, with a nano-scale particle size. According to varying synthesis conditions, the particle size of the nano-scaled platinum group metal active component is in the range of 0.5-10 nm, preferably in the range of 1-8 nm, more preferably in the range of 1-5 nm.

According to the common general knowledge in the art, the metal-organic framework compounds are coordination polymers formed by one or more polydentate organic ligands containing oxygen, nitrogen and the like (mostly, aromatic polyacid and polybase) with one or more transition metal ions, mostly having a high porosity and a good chemical stability.

In one embodiment, the percentage content of the nano-scaled platinum group metal active component is 0.1-1%, by mass of the carrier.

In one embodiment, said catalyst further comprises a promoter, and the percentage content of metal element in the promoter is 20% or less, by mass of the carrier.

In one embodiment, said catalyst further comprises a promoter, and the percentage content of metal element in the promoter is 1-10%, by mass of the carrier.

In one embodiment, said promoter is one metal or a mixture of two or more metals optionally selected from iron, cobalt, nickel and copper.

In one embodiment, said promoter is one or more oxides optionally selected from iron oxides, cobalt oxides, nickel oxide and copper oxides.

In one embodiment, said carrier is alumina and/or magnesia.

In the present application, the calculating method for the percentage content of the nano-scaled platinum group metal active component by mass of the carrier is as followed, (mass of the platinum group metal in the catalyst/mass of the carrier)×100%.

In the present application, the calculating method for the percentage content of metal element in the promoter by mass of the carrier is as followed, (mass of the metal element in the promoter/mass of the carrier)×100%.

The present application also discloses a method for preparing said supported nano-scaled platinum group metal heterogeneous catalyst characterized in comprising the steps as follows:

a) placing said carrier into a solution containing a platinum group metal salt, mixing uniformly, removing the solvent in the presence of ultrasound wave; said solvent is preferably water and/or ethanol; the mass ratio of the platinum group metal element to the carrier is 0.01-2:100, preferably 0.1-1:100;

b) drying the sample obtained from step a) at 100-200° C. for 1-20 hours, and calcining at 200-600° C. for 1-20 hours;

c) adding the sample obtained from step b) into a mixed solution of a reductant, a capping agent, and a stabilizer, and carrying out a reduction reaction at 20-120° C.;

d) washing and drying the sample obtained from step c) in vacuum to obtain said supported nano-scaled platinum group metal heterogeneous catalyst.

In one embodiment, the method comprises the following steps:

a) placing said carrier into a solution containing a promoter metal salt and a solvent, standing for 1-20 hours, drying and calcining; said solvent is preferably water and/or ethanol; the mass ratio of the promoter metal element to the carrier in the solution is not more than 1:5, preferably 1-10:100;

b) placing the sample obtained from step a) into a solution containing a platinum group metal salt and a solvent, mixing uniformly, removing the solvent in the presence of ultrasound wave; said solvent is preferably water and/or ethanol; the mass ratio of the platinum metal element to the carrier in the solution is 0.01-2%, preferably 0.1-1%;

c) drying the sample obtained from step b) at 100-200° C. for 1-20 hours, and calcining at 200-600° C. for 1-20 hours;

d) adding the sample obtained from step c) into a mixed solution of a reductant, a capping agent, and a stabilizer, and carrying out the reduction reaction at 20-120° C.; and e) washing and drying the sample obtained from step d) in vacuum to obtain said supported nano-scaled platinum group metal heterogeneous catalyst.

In one embodiment, in the process of removing the solvent in the solution containing the platinum group metal salt in the presence of ultrasonic wave, a heating means may be used simultaneously.

In one embodiment, said promoter metal salt is one or more salts selected from nitrates, acetates, and halides of iron, cobalt, nickel and copper.

In one embodiment, said platinum group metal salt is one or more salts selected from acetates, nitrates, halides and acetyl acetonates of a platinum group metal.

Said reductant is an agent having a reducing effect commonly used in the art. In one embodiment, the reductant is one or more optionally selected from sodium borohydride, hydrazine hydrate, ascorbic acid, formaldehyde, formic acid, sodium formate, sodium acetate, glucose, and ethylene glycol.

Said capping agent is an agent having a structure directing effect used in the art. In one embodiment, the capping agent is one or more optionally selected from sodium chloride, potassium chloride, sodium bromide, potassium bromide, sodium iodide, potassium iodide, citric acid, sodium citrate, potassium citrate, and ammonium citrate.

Said stabilizer is an agent having a protective effect used in the art. In one embodiment, the stabilizer is one or more optionally selected from polyvinylpyrrolidone, cetyl trimethyl ammonium bromide, cetyl trimethyl ammonium chloride, and poly(ethylene oxide)-poly(propylene oxide)-poly(ethylene oxide) triblock copolymer.

In one embodiment, in the reduction step of said catalyst preparation method, the mass ratio of the reductant, the capping agent, and the stabilizer to the carrier is 1-400:10-100:20-400:100. A person skilled in the art may choose appropriate conditions according to actual production requirements within the abovementioned ranges.

In one embodiment, the method comprises the following steps:

a) said carrier is impregnated into an aqueous or ethanol solution of a platinum group metal salt (any compound selected from acetates, nitrates, halides and acetylacetonates or a combination of any compounds therein), stirred uniformly, so that the carrier is uniformly dispersed into the solution of the platinum group metal salt;

b) the mixing solution of the platinum group metal salt and the carrier from step a) is subjected to ultrasound wave under heating condition to evaporate the solvent to dryness, so that the platinum group metal salt is uniformly adsorbed to the surface of the carrier;

c) the resulting adsorption sample from step b) is dried at 100-200° C. for 20 hours, and then calcined at 200-600° C. for 1-20 hours;

d) the resulting sample from step c) is added a reductant (any compound of sodium borohydride, hydrazine hydrate, ascorbic acid, formaldehyde, formic acid, sodium formate, sodium acetate, glucose, and ethylene glycol, or a combination of any compounds therein), a capping agent (any compound of sodium chloride, potassium chloride, sodium bromide, potassium bromide, sodium iodide, potassium iodide, citric acid, sodium citrate, potassium citrate, and ammonium citrate, or a combination of any compounds therein) and a stabilizer (any compound of polyvinylpyrrolidone, cetyl trimethyl ammonium bromide, cetyl trimethyl ammonium chloride, and poly(ethylene oxide)-poly(propylene oxide)-poly(ethylene oxide) triblock copolymers or a combination of any compounds therein) and subjected to a reducing reaction, with the ratio of the capping agent to the stabilizer being from 1:2-4 and the reduction temperature of 20-120° C.; and e) the resulting sample from step d) is filtered, washed, and placed into a vacuum drying oven to be dried for 1-20 hours so as to obtain a supported nano-scaled platinum group metal heterogeneous catalyst.

In one embodiment, the method comprises the following steps:

a) said carrier is impregnated into an aqueous solution or ethanol solution of a promoter metal salt, after standing for 1-20 hours, dried at 100-200° C. for 1-20 hours, then calcined at 200-600° C. for 1-20 hours;

b) the resulting sample from step a) is impregnated into an aqueous solution or ethanol solution of a platinum group metal salt (any compound of acetates, nitrates, halides and acetylacetonates or a combination of any compounds therein), stirred uniformly, so that the carrier is uniformly dispersed into the solution of the platinum group metal salt;

c) the mixture solution obtained from step b) is subjected to ultrasound wave under a heating condition to volatilize the solvent to dryness, so that the platinum group metal salt is uniformly absorbed to the surface of the carrier;

d) the absorbed sample obtained from step c) is dried at 100-200° C. for 1-20 hours, and then calcined at 200-600° C. for 1-20 hours;

e) the sample obtained from step d) is added a reductant (any compound of sodium borohydride, hydrazine hydrate, ascorbic acid, formaldehyde, formic acid, sodium formate, sodium acetate, glucose, and ethylene glycol, or a combination of any compounds therein), a capping agent (any compound of sodium chloride, potassium chloride, sodium bromide, potassium bromide, sodium iodide, potassium iodide, citric acid, sodium citrate, potassium citrate, and ammonium citrate, or a combination of any compounds therein), and a stabilizer (any compound of polyvinylpyrrolidone, cetyl trimethyl ammonium bromide, cetyl trimethyl ammonium chloride, and poly(ethylene oxide)-poly(propylene oxide)-poly(ethylene oxide) triblock copolymers, or a combination of any compounds therein) and subjected to a reducing reaction, with the ratio of the capping agent to the stabilizer being from 1:2-4 and the reduction temperature of 20-120° C.; and f) the sample obtained from step e) is filtered, washed, and placed into a vacuum drying oven to be dried for 1-20 hours so as to obtain a supported nano-scaled platinum group metal heterogeneous catalyst.

In the technical solution disclosed in the present application, the ultrasonic frequency used is 20 KHz or more; preferably a frequency of 20-200 KHz. A person skilled in the art may select the appropriate ultrasonic frequency according to general knowledge.

According to the technical solution disclosed herein, a person skilled in the art has a motivation to achieve desired technical effects by selecting the types of the platinum group metal salts and the promoter metal salts; varying the ratio of the active component of the catalyst and the promoter; choosing the kinds and proportions of suitable reductants, capping agents, stabilizers, and the reduction temperature to achieve the desired technical effect, depending on the requirements of actual production.

The advantageous effects of the invention are as followed.

1. The used platinum group metal heterogeneous catalyst has low requirements for the purity of feed gas, which will sharply reduce equipment investment.

2. Supported nano-scaled platinum group metal heterogeneous catalyst has no corrosion to the equipment.

3. The employment of fixed bed reaction process makes easy separation of the catalyst from the products.

4. The conversion of CO and selectivity for methyl formate are both high.

5. The reaction conditions are mild and easy to operate.

6. No toxic and harmful substances to be emitted, which is environmentally friendly.

DESCRIPTION OF ACCOMPANYING FIGURES

SPECIFIC EMBODIMENTS FOR CARRYING OUT THE INVENTION

Figure 1:
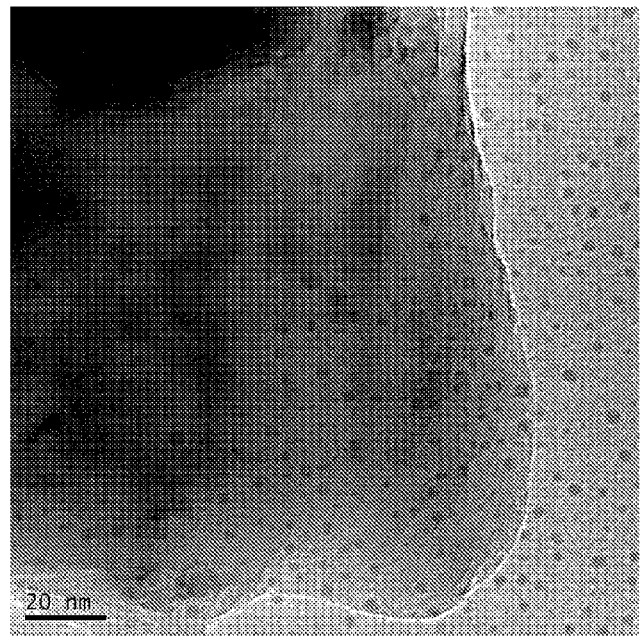
FIG. 1 is a transmission electron micrograph image of catalyst 5 in 20 nm-scale.

The invention is described in detail by the following examples, but the present invention is not limited to these examples.

The raw materials and reagents used in the examples were purchased commercially, applied directly without any special treatment.

Example 1: Preparation of Catalyst 1

1 g of alumina was weighed, impregnated into 15 mL ethanol solution of 50 mmol/L $CuCl_2.2H_2O$, stood for 18 hours, dried at 100° C. for 15 hours, calcined at 400° C. for 5 hours, then impregnated again into 1.25 mL aqueous solution of 37.6 mmol/L potassium chloropalladite, and 4 mL water was added, stirred for 3 hours, dispersed ultrasonically for 3 hours, dried at 120° C. for 15 hours, calcined at 400° C. for 5 hours, added with 0.1 g of ascorbic acid, 0.2 g of citric acid and 0.5 g of polyvinylpyrrolidone, reduced at 90° C. for 1 hour, dried in vacuum at 60° C. for 15 hours, to obtain Pd—Cu/$Al_2O_3$ catalyst 1 for use in the reaction of vapor-phase methanol carbonylation to methyl formate.

Example 2: Preparation of Catalyst 2

1 g of alumina was weighed, impregnated into 15 mL ethanol solution of 50 mmol/L $CuCl_2.2H_2O$, stood for 18 hours, dried at 100° C. for 15 hours, calcined at 400° C. for 5 hours, then impregnated again into 0.68 mL aqueous solution of 37.6 mmol/L chloroplatinic acid, and 4 mL water was added, stirred for 3 hours, dispersed ultrasonically for 3 hours, dried at 120° C. for 15 hours, calcined at 400° C. for 5 hours, added with 0.1 g of ascorbic acid, 0.2 g of citric acid and 0.5 g of polyvinylpyrrolidone, reduced at 90° C. for 1 hour, dried in vacuum at 60° C. for 15 hours, to obtain Pd—Cu/$Al_2O_3$ catalyst 2 for use in the reaction of vapor-phase methanol carbonylation to methyl formate.

Example 3: Preparation of Catalyst 3

1 g of magnesia was weighed, impregnated into 17 mL ethanol solution of 50 mmol/L $Ni(NO_3)_2.6H_2O$, stood for 18 hours, dried at 100° C. for 15 hours, calcined at 400° C. for 5 hours, then impregnated again into 0.63 mL aqueous solution of 37.6 mmol/L potassium chloropalladite, and 4 mL water was added, stirred for 3 hours, dispersed ultrasonically for 3 hours, dried at 120° C. for 15 hours, calcined at 400° C. for 5 hours, added with 0.1 mL formaldehyde, 0.24 g of sodium citrate and 0.6 g of poly(ethylene oxide)-poly(propylene oxide)-poly(ethylene oxide) triblock copolymer, reduced at 100° C. for 2 hours, dried in vacuum at 60° C. for 15 hours, to obtain PtPd—Ni/MgO catalyst 3 for use in the reaction of vapor-phase methanol carbonylation to methyl formate.

Example 4: Preparation of Catalyst 4

1 g of magnesia was weighed, impregnated into 17 mL ethanol solution of 50 mmol/L $Ni(NO_3)_2.6H_2O$, stood for 18 hours, dried at 100° C. for 15 hours, calcined at 400° C. for 5 hours, then impregnated again into a mixing aqueous solution of 0.65 mL 37.6 mmol/L rhodium chloride hydrate and 0.34 mL 37.6 mmol/L chloroplatinic acid, and 4 mL water was added, stirred for 3 hours, dispersed ultrasonically for 3 hours, dried at 120° C. for 15 hours, calcined at 400° C. for 5 hours, added with 1 mL formaldehyde, 0.24 g of sodium citrate and 0.6 g of poly(ethylene oxide)-poly(propylene oxide)-poly(ethylene oxide) triblock copolymer, reduced at 100° C. for 2 hours, dried in vacuum at 60° C. for 15 hours, to obtain PtRh—Ni/MgO catalyst 4 for use in the reaction of vapor-phase methanol carbonylation to methyl formate.

Example 5: Preparation of Catalyst 5

1 g of alumina was weighed, impregnated into 1.25 mL aqueous solution of 37.6 mmol/L potassium chloropalladite, and 4 mL water was added, stirred for 3 hours, dispersed ultrasonically for 3 hours, dried at 120° C. for 15 hours, calcined at 400° C. for 5 hours, added with 0.1 g of ascorbic acid, 0.2 g of citric acid and 0.5 g of polyvinylpyrrolidone, reduced at 90° C. for 1 hour, dried in vacuum at 60° C. for 15 hours, to obtain Pd/$Al_2O_3$ catalyst 5 for use in the reaction of vapor-phase methanol carbonylation to methyl formate.

Example 6: Preparation of Catalysts 6 to 11

1 g of carrier was weighed, impregnated into 2 mL solution containing platinum group metal salts, then added with 4 mL water, stirred for 3 hours, dispersed ultrasonically for 3 hours, dried at 120° C. for 15 hours, calcined at 400° C. for 5 hours, and added with an amount of a reductant, a capping agent and a stabilizer, reduced at 90° C. for 1 hour, dried in vacuum at 60° C. for 15 hours, to obtain catalyst 6 to catalyst 11. The numbers and specific preparation conditions of the catalysts are shown in Table 1.

TABLE 1

| | | Conditions for preparation of catalyst 6~catalyst 11 | | |
|---|---|---|---|---|
| | | Solutions of platinum group metal salts | | |
| Numbers of samples | Carriers | Solutes and solvent in solutions | Mass of platinum group elements in solutions | Types and added amounts of reductant, capping agent and stabilizer |
| Catalyst 6 | zirconia | Aqueous solution of ruthenium nitrate | Ruthenium: 0.0001 g | Sodium borohydride 0.01 g, sodium chloride 0.1 g, cetyl trimethyl ammonium bromide 0.3 g |

TABLE 1-continued

Conditions for preparation of catalyst 6~catalyst 11

| Numbers of samples | Carriers | Solutes and solvent in solutions | Mass of platinum group elements in solutions | Types and added amounts of reductant, capping agent and stabilizer |
|---|---|---|---|---|
| Catalyst 7 | titanium dioxide | Hydrochloric acid solution of iridium trichloride | Iridium: 0.001 g | Hydrazine hydrate 0.01 g, KCl 0.1 g, cetyl trimethyl ammonium chloride 0.3 g |
| Catalyst 8 | silicon dioxide | Aqueous solution of osmium trichloride | Osmium: 0.01 g | formic acid 2 mL, sodium bromide 0.4 g, polyvinyl pyrrolidone 1 g |
| Catalyst 9 | zinc oxide | Hydrochloric acid solution of iridium trichloride and osmium trichloride | Iridium: 0.01 g Osmium: 0.005 g | (Sodium formate 0.1 g + sodium acetate 0.1 g), potassium bromide 0.4 g, cetyl trimethyl ammonium bromide 1 g |
| Catalyst 10 | Activated carbon | Ethanol solution of palladium chloride | Palladium: 0.012 g | Glucose 2 g, sodium iodide, 0.5 g, Polyvinylpyrrolidone 2 g |
| Catalyst 11 | 0.5 g alumina + 0.5 g zinc oxide | Aqueous solution of sodium hexachlororhodate | Rhodium: 0.02 g | Ethylene glycol 4 g, potassium iodide 1 g, cetyl trimethyl ammonium chloride 3 g |

Example 7: Preparations of Catalysts 12-17

1 g of carrier was weighed, placed into 17 mL solution containing promoter metal salts, stood for 18 hours, dried at 100° C. for 15 hours, calcined at 400° C. for 5 hours, then again impregnated into 2 mL solution containing platinum metal salts, again added with 4 mL water, stirred for 3 hours, dispersed ultrasonically for 3 hours, dried at 120° C. for 15 hours, calcined at 400° C. for 5 hours, and added with an amount of a reductant, a capping agent and a stabilizer, reduced at 100° C. for 1 hour, dried in vacuum at 60° C. for 15 hours, to obtain catalyst 12 to catalyst 17. The numbers and specific preparation conditions of the catalysts are shown in Table 2.

TABLE 2

Conditions for preparation of catalyst 12~catalyst 17

| | | Solution containing promoter metal salts | | Solution containing platinum group metal salts | | |
|---|---|---|---|---|---|---|
| Number | Carriers | Solutes and solvents in solutions | Mass of promoter metal elements | Solutes and solvents in solutions | Mass of platinum group metal elements in solutions | Types and added amounts of reductant, capping agent and stabilizer |
| Catalyst 12 | Zirconia | Aqueous solution of ferric chloride | Iron: 0.005 g | Aqueous solution of ruthenium nitrate | Ruthenium: 0.0001 g | Sodium borohydride 0.01 g, sodium chloride 0.1 g, cetyl trimethyl ammonium bromide 0.3 g |
| Catalyst 13 | Titanium dioxide | Aqueous solution of cobalt chloride | Cobalt: 0.01 g | Hydrochloric acid solution of iridium trichloride | Iridium: 0.001 g | Hydrazine hydrate 0.01 g, KCl 0.1 g, cetyl trimethyl ammonium chloride 0.3 g |
| Catalyst 14 | Silica | Ethanol solution of copper nitrate and nickel chloride | Cooper: 0.04 g Nickel: 0.04 g | Aqueous solution of osmium trichloride | Osmium: 0.01 g | Formic Acid 2 mL, sodium bromide 0.4 g, polyvinyl pyrrolidone 1 g |
| Catalyst 15 | Zinc oxide | Ethanol solution of nickel nitrate | Nickel: 0.1 g | Hydrochloric acid solution of iridium trichloride and osmium trichloride | Iridium: 0.01 g Osmium: 0.005 g | (Sodium formate 0.1 g + sodium acetate, 0.1 g), potassium bromide 0.4 g, cetyl trimethyl ammonium bromide 1 g |

TABLE 2-continued

Conditions for preparation of catalyst 12~catalyst 17

| Number | Carriers | Solution containing promoter metal salts | | Solution containing platinum group metal salts | | Types and added amounts of reductant, capping agent and stabilizer |
|---|---|---|---|---|---|---|
| | | Solutes and solvents in solutions | Mass of promoter metal elements | Solutes and solvents in solutions | Mass of platinum group metal elements in solutions | |
| Catalyst 16 | Activated Carbon | Aqueous solution of copper chloride, cobalt chloride and iron chloride | Copper: 0.05 g Cobalt: 0.05 g Iron: 0.05 g | Ethanol solution of palladium chloride | Palladium: 0.012 g | Glucose 2 g, sodium iodide 0.5 g, Polyvinylpyrrolidone 2 g |
| Catalyst 17 | 0.5 g alumina + 0.5 g zinc oxide | Aqueous solution of cobalt chloride | Cobalt: 0.2 g | Aqueous solution of sodium hexachlororhodate | Rhodium: 0.02 g | Ethylene glycol 4 g, potassium iodide 1 g, cetyl trimethyl ammonium chloride 3 g |

Figure 2:
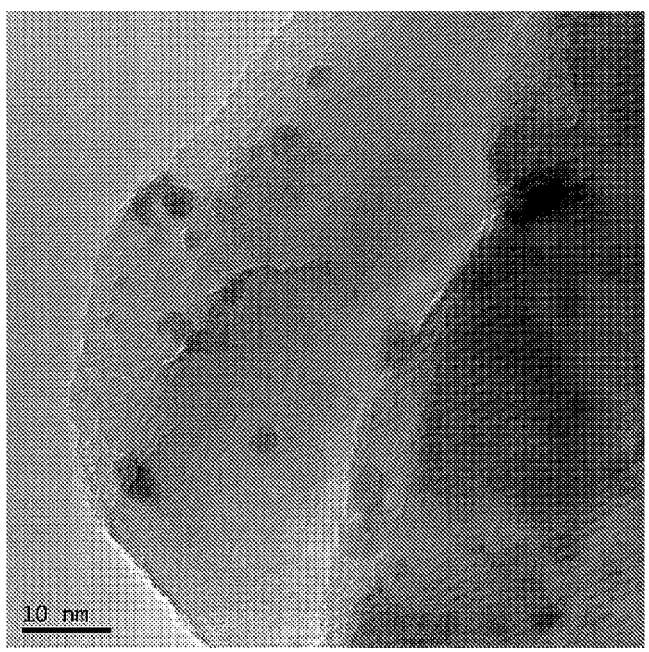
FIG. 2 is a transmission electron micrograph image of catalyst 5 in 10 nm-scale.

Example 8: Transmission Electron Micrograph (TEM) Characterization of Catalysts Catalysts 1 to 17 were characterized by TEM using Tecnai F20, FEI. The resulting TEM images showed that the platinum group metal as active center was uniformly distributed on the carrier, with particle size distribution in the range between 0.5-10 nm, more focused distribution in the range of 1-8 nm, further focused in the range of 1-5 nm. Wherein, a typical TEM image is represented by catalyst 5, as shown in FIG. 1 and FIG. 2. As seen from FIG. 1, as the active center, the particles of palladium are relatively uniform, with the range of particle size focused in 1-5 nm; as seen from FIG. 2, the range of particle size distribution of the palladium active component is also between 1-5 nm.

Example 9: Performance Evaluation of Catalysts 1-5

Catalysts 1-5 were loaded into a fixed bed reactor used in the reaction of vapor-phase methanol carbonylation to methyl formate, with a ratio of $CH_3OH:CO:H_2:O_2$ in feed gas being 18:18:9:5 (volume ratio), a space velocity of 2000 $h^{-1}$, a reaction temperature of 100° C., and a reaction pressure of 0.1 MPa. The purity of $CH_3OH$ is chemical purity, and the purity of CO, $H_2$ and $O_2$ is 99.9%, the reaction results are shown in Table 3.

TABLE 3

Catalytic performances of catalysts 1~5 in the reaction of vapor-phase methanol carbonylation to methyl formate

| Catalyst | Conversion of CO (%) | Selectivity for methyl formate (%) | Space-time yield of methyl formate $(g \cdot L^{-1} \cdot h^{-1})$ |
|---|---|---|---|
| Catalyst 1 | 75 | 92 | 1376 |
| Catalyst 2 | 82 | 94 | 1537 |
| Catalyst 3 | 87 | 99 | 1718 |
| Catalyst 4 | 93 | 99 | 1836 |
| Catalyst 5 | 70 | 95 | 1326 |

Example 10: Performance Evaluation of Catalysts 6-17

The resulting catalysts 6-17 were loaded into a fixed bed reactor used in the reaction of vapor-phase methanol carbonylation to methyl formate. The reaction conditions and the reaction results are shown in Table 4.

TABLE 4

Reaction conditions and catalytic performances of Catalyst 6~Catalyst 17 in the reaction of vapor-phase methanol carbonylation to methyl formate

| | Reaction conditions | | | | | Results of reactions | |
|---|---|---|---|---|---|---|---|
| Catalysts | Percentage content of methanol, carbon monoxide, hydrogen and oxygen in feed gas, by volume | Space velocity $(h^{-1})$ | Temperature (° C.) | Presure (MPa) | Conversion of CO (%) | Selectivity for methyl formate (%) | Space-time yield of methyl formate $(g \cdot L^{-1} \cdot h^{-1})$ |
| Catalyst 6 | 20%, 50%, 20%, 10% | 500 | 50 | 0.01 | 5 | 80 | 27 |
| Catalyst 7 | 30%, 40%, 15%, 15% | 1000 | 80 | 0.08 | 12 | 82 | 105 |
| Catalyst 8 | 40%, 40%, 10%, 10% | 2000 | 100 | 0.1 | 18 | 70 | 270 |
| Catalyst 9 | 50%, 30%, 10%, 10% | 3000 | 150 | 1 | 27 | 75 | 488 |
| Catalyst 10 | 50%, 20%, 25%, 5% | 4000 | 50 | 1.5 | 60 | 95 | 1221 |
| Catalyst 11 | 40%, 10%, 30%, 20% | 5000 | 80 | 2 | 75 | 90 | 904 |
| Catalyst 12 | 20%, 50%, 20%, 10% | 2200 | 100 | 0.01 | 8 | 81 | 191 |
| Catalyst 13 | 30%, 40%, 15%, 15% | 2300 | 150 | 0.08 | 17 | 84 | 352 |

TABLE 4-continued

Reaction conditions and catalytic performances of Catalyst 6~Catalyst 17 in the reaction of vapor-phase methanol carbonylation to methyl formate

| Catalysts | Reaction conditions | | | | Results of reactions | | |
|---|---|---|---|---|---|---|---|
| | Percentage content of methanol, carbon monoxide, hydrogen and oxygen in feed gas, by volume | Space velocity ($h^{-1}$) | Temperature (° C.) | Presure (MPa) | Conversion of CO (%) | Selectivity for methyl formate (%) | Space-time yield of methyl formate ($g \cdot L^{-1} \cdot h^{-1}$) |
| Catalyst 14 | 40%, 40%, 10%, 10% | 3000 | 50 | 0.1 | 24 | 73 | 563 |
| Catalyst 15 | 50%, 30%, 10%, 10% | 3500 | 80 | 1 | 33 | 78 | 724 |
| Catalyst 16 | 50%, 20%, 25%, 5% | 4000 | 100 | 1.5 | 67 | 97 | 1393 |
| Catalyst 17 | 40%, 10%, 30%, 20% | 5000 | 150 | 2 | 81 | 92 | 998 |

The above description is only several examples of the invention, without limiting the invention in any way. Although the invention is disclosed by the preferred examples as above, they are not used for limiting the invention. Various alternations or modifications made by a person skilled in the art utilizing the above disclosed technical contents without departing the scope of the technical solution of the invention are all equivalent embodiments, which belong to the scope of the technical solution of the invention.

The invention claimed is:

1. A process for vapor-phase carbonylation of methanol to methyl formate, in which a feed gas containing methanol, carbon monoxide, hydrogen and oxygen is passed through a reactor loaded with a supported nano-scaled platinum group metal heterogeneous catalyst to produce methyl formate by a vapor-phase carbonylation reaction, under reaction conditions with a gas hourly space velocity of 500-5000 h–1, a temperature of 50-150° C. and a pressure of 0.01-2 MPa,
wherein the supported nano-scaled platinum group metal heterogeneous catalyst comprises a nano-scaled platinum group metal active component and a carrier, wherein,
the percentage content of the nano-scaled platinum group metal active component is 0.01-2% by mass of the carrier;
said nano-scaled platinum group metal active component is one metal or a mixture of two or more metals selected from ruthenium, rhodium, palladium, osmium, iridium, and platinum, or an alloy of two or more metals selected from ruthenium, rhodium, palladium, osmium, iridium, and platinum;
said carrier is one or more selected from alumina, silica, magnesia, zinc oxide, zirconia, titania, metal-organic framework compounds, activated carbon, molecular sieves, carbon nanotubes, and graphene; and
wherein said feed gas comprises 10-50% by volume of methanol, 10-50% by volume of carbon monoxide, 10-30% by volume of hydrogen, and 5-20% by volume of oxygen.

2. The process according to claim 1, in which said reactor is a fixed bed reactor or multiple fixed bed reactors connected in series and/or in parallel manner.

3. The process according to claim 1, wherein the particle size of said nano-scaled platinum group metal active component is 0.5-10 nm.

4. The process according to claim 1, wherein the supported nano-scaled platinum group metal heterogeneous catalyst further comprises a promoter, wherein,
the percentage content of metal elements in the promoter is 20% or less by mass of the carrier; and
said promoter is one metal or a mixture of two or more metals selected from iron, cobalt, nickel and copper; or one or more oxides selected from iron oxides, cobalt oxides, nickel oxide and copper oxides.

5. The process according to claim 1, wherein the supported nano-scaled platinum group metal heterogeneous catalyst is prepared by a method comprising the steps as follows:
a) placing a carrier into a solution containing a platinum group metal salt and a solvent, mixing uniformly, and ultrasonically dispersing the solution containing the platinum group metal salt onto the carrier;
b) drying the sample obtained from step a) at 100-200° C. for 1-20 hours, and calcining at 200-600° C. for 1-20 hours;
c) adding the sample obtained from step b) into a solution comprising a reductant, a capping agent, and a stabilizer, and carrying out a reduction reaction at 20-120° C.; and
d) washing and drying the sample obtained from step c) in vacuum to obtain said supported nano-scaled platinum group metal heterogeneous catalyst.

6. The process according to claim 5, wherein the catalyst further comprises a promotor, wherein,
the percentage content of metal elements in the promoter is 20% or less by mass of the carrier; and
said promoter is one metal or a mixture of two or more metals selected from iron, cobalt, nickel and copper; or one or more oxides selected from iron oxides, cobalt oxides, nickel oxide and copper oxides; and
the carrier is treated as follows before used in step a):
placing a carrier into a solution containing a promoter metal salt, standing for 1-20 hours, drying and calcining; and said promoter metal salt being one or more selected from nitrates, acetates, and halides of iron, cobalt, nickel and copper.

7. The process according to claim 5, wherein said platinum group metal salt is one or more selected from acetates, nitrates, halides and acetyl acetonates of a platinum group metal.

8. The process according to claim 5, wherein said reductant is one or more selected from sodium borohydride, hydrazine hydrate, ascorbic acid, formaldehyde, formic acid, sodium formate, sodium acetate, glucose, and ethylene glycol; said capping agent is one or more selected from sodium chloride, potassium chloride, sodium bromide, potassium bromide, sodium iodide, potassium iodide, citric acid, sodium citrate, potassium citrate, and ammonium citrate; and said stabilizer is one or more selected from polyvinylpyrrolidone, cetyl trimethyl ammonium bromide, cetyl trimethyl ammonium chloride, and poly(ethylene oxide)-poly(propylene oxide)-poly(ethylene oxide) triblock copolymer.

9. The process according to claim 6, wherein said platinum group metal salt is one or more selected from acetates, nitrates, halides and acetyl acetonates of a platinum group metal.

10. The process according to claim 6, wherein said reductant is one or more selected from sodium borohydride, hydrazine hydrate, ascorbic acid, formaldehyde, formic acid, sodium formate, sodium acetate, glucose, and ethylene glycol; said capping agent is one or more selected from sodium chloride, potassium chloride, sodium bromide, potassium bromide, sodium iodide, potassium iodide, citric acid, sodium citrate, potassium citrate, and ammonium citrate; and said stabilizer is one or more selected from polyvinylpyrrolidone, cetyl trimethyl ammonium bromide, cetyl trimethyl ammonium chloride, and poly(ethylene oxide)-poly(propylene oxide)-poly(ethylene oxide) triblock copolymer.

\* \* \* \* \*